(12) United States Patent
Bernet et al.

(10) Patent No.: US 9,512,957 B2
(45) Date of Patent: *Dec. 6, 2016

(54) ANALYZER ASSEMBLY PLATFORM

(71) Applicant: Roche Molecular Systems, Inc., Pleasanton, CA (US)

(72) Inventors: Roland Bernet, Immensee (CH); Harald Ferihumer, Rothenburg (CH); Marcel Kaeppeli, Merenschwand (CH); Raymond Ochsenbein, Zurich (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/978,518

(22) Filed: Dec. 22, 2015

(65) Prior Publication Data

US 2016/0109055 A1  Apr. 21, 2016

Related U.S. Application Data

(62) Division of application No. 13/050,131, filed on Mar. 17, 2011, now Pat. No. 9,310,390.

(30) Foreign Application Priority Data

Mar. 17, 2010 (EP) ...................................... 10156795

(51) Int. Cl.
*G01N 35/00* (2006.01)
*G01N 35/02* (2006.01)
*F16M 11/24* (2006.01)
*F16M 11/04* (2006.01)
*F16M 11/18* (2006.01)
*G01N 1/40* (2006.01)

(52) U.S. Cl.
CPC ............ *F16M 11/24* (2013.01); *F16M 11/043* (2013.01); *F16M 11/18* (2013.01); *G01N 1/40* (2013.01); *G01N 1/405* (2013.01); *G01N 35/02* (2013.01); *G01N 2035/00326* (2013.01); *Y10T 29/49826* (2015.01)

(58) Field of Classification Search
None
See application file for complete search history.

(56) References Cited

U.S. PATENT DOCUMENTS

| 4,002,383 A | 1/1977 | Holloway |
| 4,115,358 A | 9/1978 | Vestergaard |
| 4,363,587 A | 12/1982 | Rooklyn |
| 5,339,749 A | 8/1994 | Hirose |

(Continued)

FOREIGN PATENT DOCUMENTS

| EP | 0707806 A2 | 4/1996 |
| EP | 0707806 A3 | 9/2000 |

(Continued)

OTHER PUBLICATIONS

Coleman et al., "Design of a large, rigid, modular optical bed for versatile optical and spectroscopic experimentation" Spectrochimica Acta, vol. 33B, pp. 127-142 (1978).

*Primary Examiner* — P. Kathryn Wright
(74) *Attorney, Agent, or Firm* — Pamela C. Ancona; David J. Chang

(57) ABSTRACT

A combination of an analytical apparatus with a platform for mounting such an apparatus comprising at least two units, and a platform on which said apparatus is mounted is disclosed, said platform comprising at least one platform element, and multiple feet for placing the platform elements on a surface. The feet are individually adjustable in height.

4 Claims, 11 Drawing Sheets

(56) References Cited

U.S. PATENT DOCUMENTS

| | | |
|---|---|---|
| 6,337,050 B1 | 1/2002 | Takahashi et al. |
| 6,447,236 B1 | 9/2002 | Grams et al. |
| 6,898,296 B2 | 5/2005 | Itoh |
| 8,226,889 B2 | 7/2012 | Nakaya |
| 2006/0083660 A1 | 4/2006 | Schorno et al. |
| 2008/0131318 A1 | 6/2008 | Nakaya |

FOREIGN PATENT DOCUMENTS

| | | |
|---|---|---|
| EP | 1582874 A1 | 10/2005 |
| EP | 1582874 B1 | 7/2008 |
| GB | 904198 | 8/1962 |
| GB | 999089 | 7/1965 |
| GB | 1231841 | 5/1971 |
| JP | 1996008887 A | 1/1996 |
| JP | 2001349897 A | 6/2000 |
| WO | 2009002357 A1 | 12/2008 |

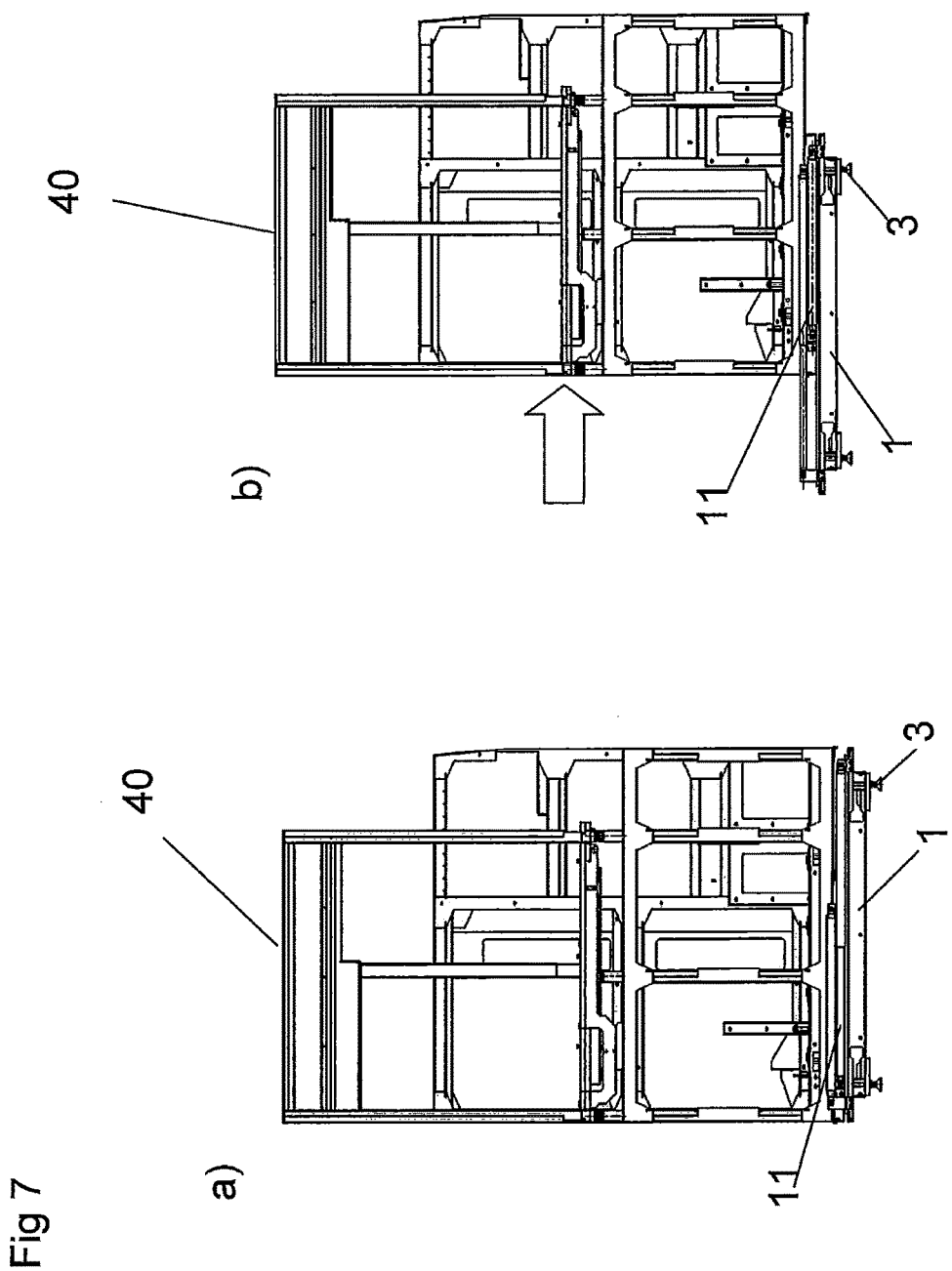

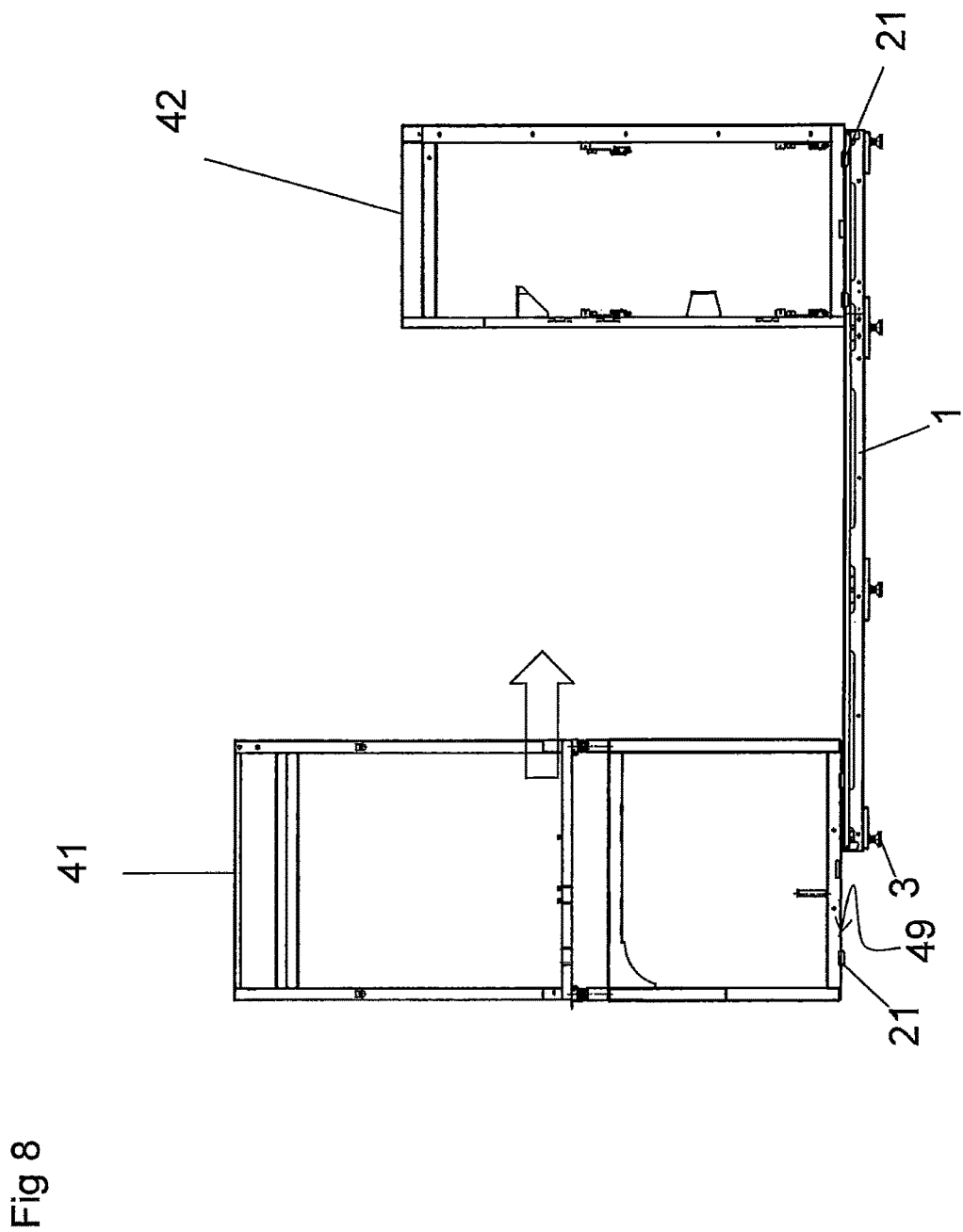

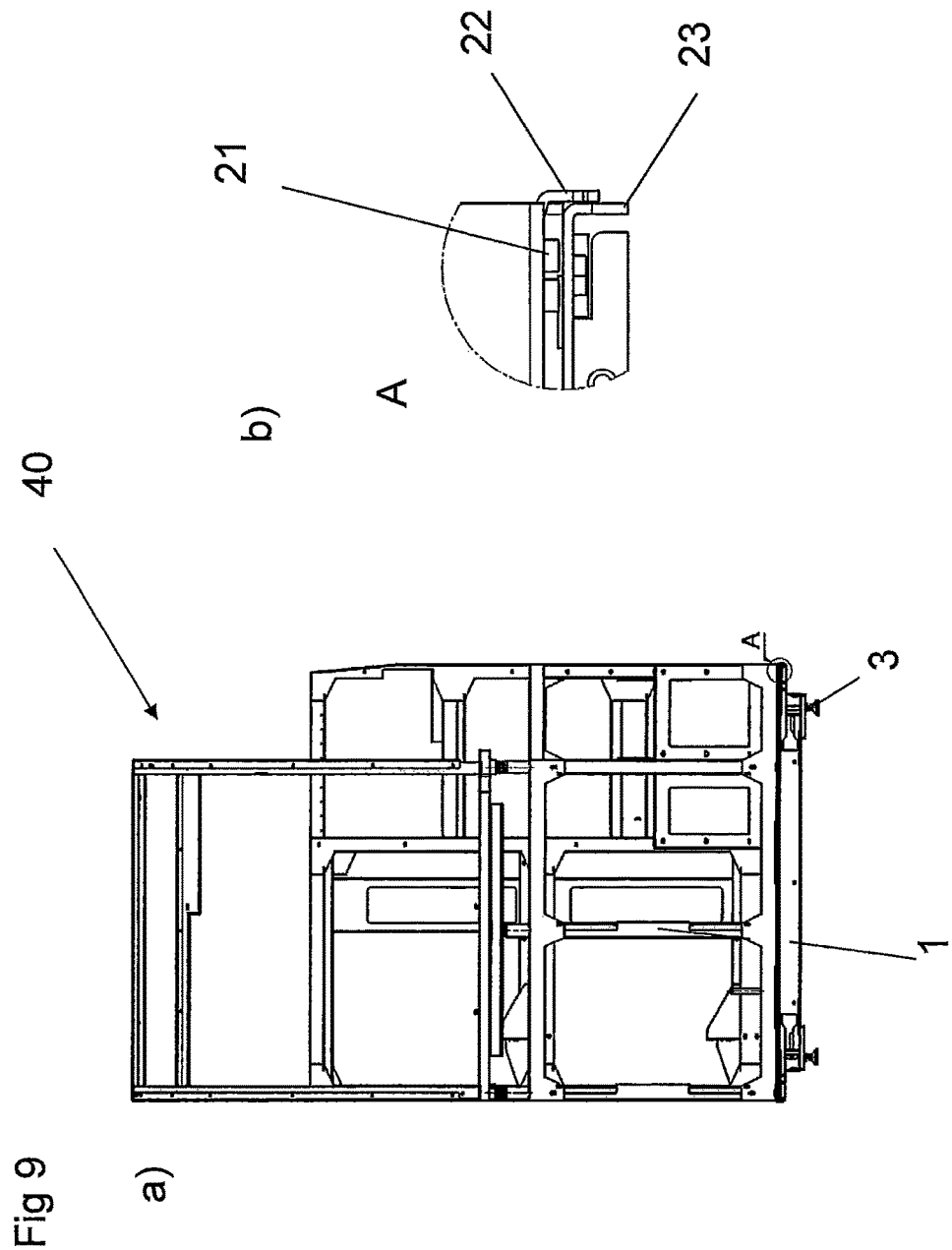

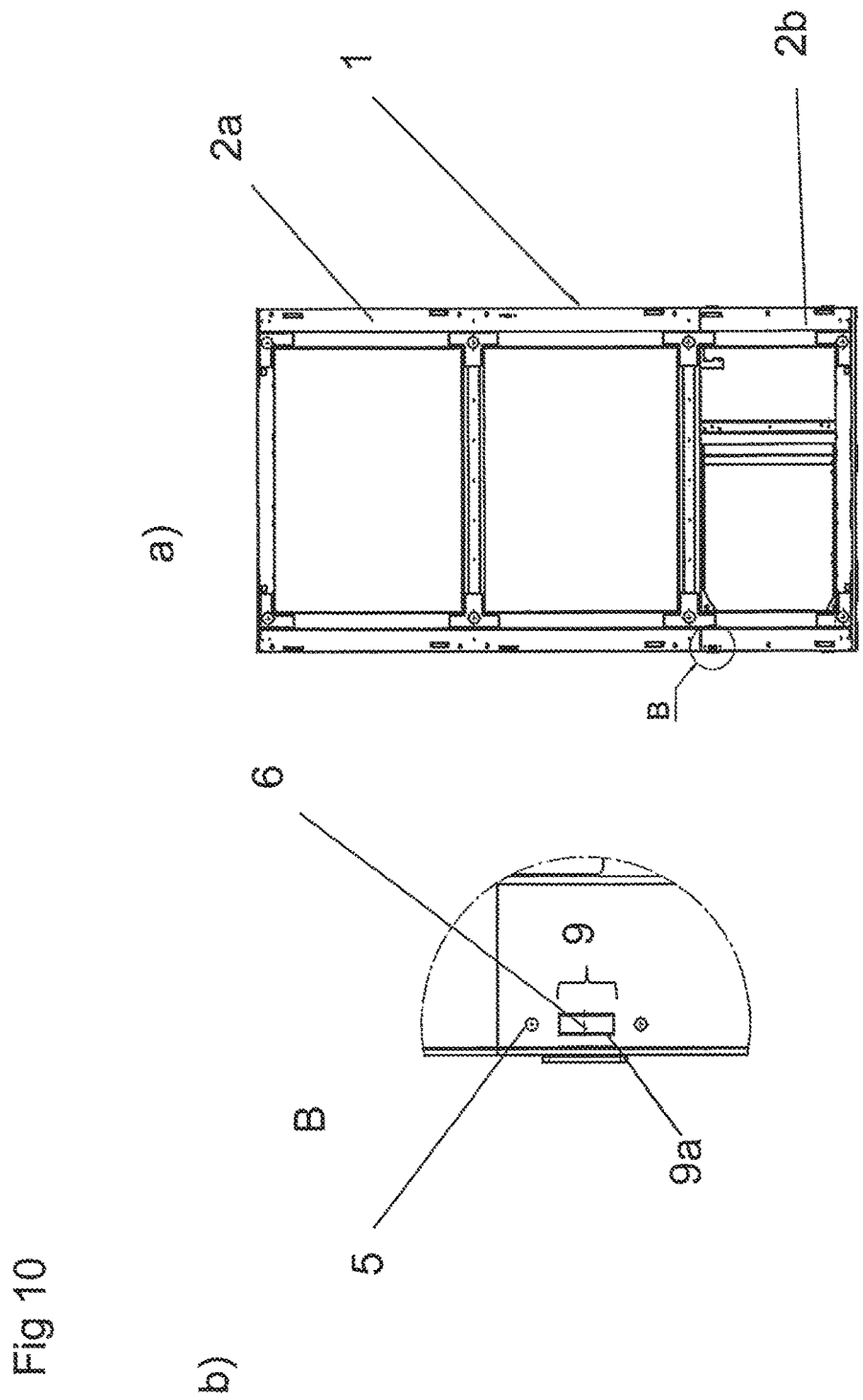

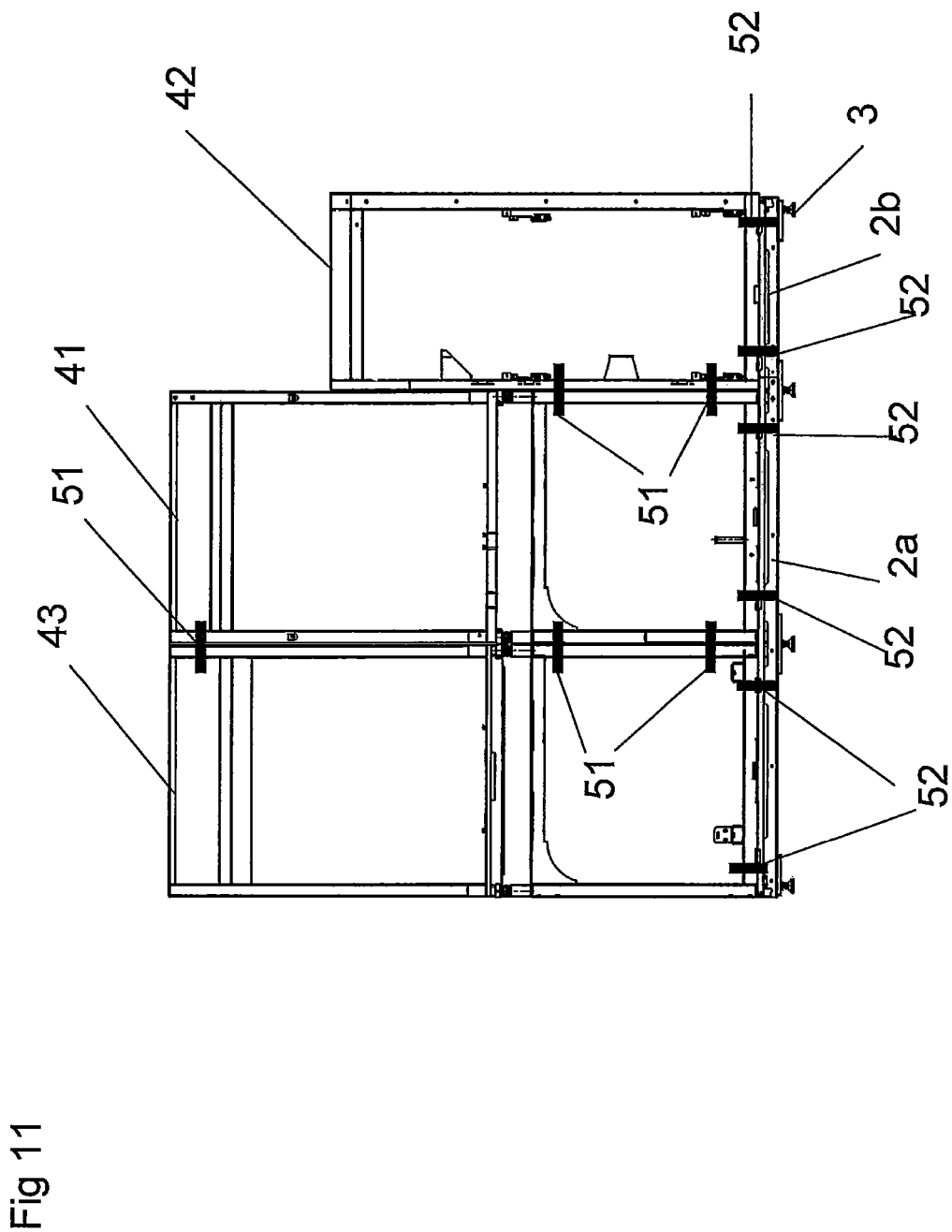

ANALYZER ASSEMBLY PLATFORM

CROSS-REFERENCES TO RELATED APPLICATIONS

The present application is a divisional of U.S. application Ser. No. 13/050,131 filed Mar. 17, 2011 which claims the benefit of priority under 35 U.S.C. §119 of EP10156795.6, filed Mar. 17, 2010, the contents of which is incorporated by reference herein in its entirety.

FIELD OF THE INVENTION

The present invention relates to analyzer assembly platforms, and more particularly to mounting of an analytical apparatus comprising at least two units.

BACKGROUND OF THE INVENTION

Multi-unit analytical apparatuses with a transport unit connecting said units require exact adjustment of each unit in both horizontal and vertical direction. Given that the surfaces on which such apparatuses are mounted are in general not planar, a mechanism is required that ensures proper positioning and, thus, proper functioning of the apparatus. Such mechanisms are described in U.S. Pat. No. 5,260,872 and U.S. Pat. No. 7,842,143 where all working stations are mounted inside one frame structure. Other mechanisms are disclosed in U.S. Pat. No. 6,337,050, WO2009/002357 and EP158287. In all of these systems, height adjustment is carried out on every individual unit with the work stations positioned on support structures.

The present invention provides for an improved method and platform for mounting an analytical apparatus comprising at least two units.

SUMMARY OF THE INVENTION

The present invention relates to a method of mounting an analytical apparatus comprising at least two units, comprising the steps of:
  placing a platform on a surface, wherein said platform comprises at least one platform element and multiple feet for placing the platform elements on a surface, wherein said feet are individually adjustable in height;
  adjusting the height of the platform assembly before mounting and positioning of the units; and
  mounting and positioning the at least two units.

The present invention further relates to a combination of an analytical apparatus comprising at least two units, and a platform on which said apparatus is mounted, said platform comprising at least one platform element and multiple feet for placing the platform elements on a surface, wherein said feet are individually adjustable in height.

The advantage of the present invention is that the method herein described allows the height adjustment of the platform before mounting of the units. Thus, height adjustment can be done more easily in the absence of the full system weight. In addition, adjustment does not need to be performed for every single unit. This results in less positioning problems between modules. The mounting method also allows for easy assembly of the units independent of the location of the system and of the laboratory surface on which the apparatus is to be mounted.

BRIEF DESCRIPTION OF THE FIGURES

FIGS. 7 a) and b) show the movement of units mounted on the second platform.

FIG. 8 shows the mounting of a second unit on a platform with one unit already mounted.

FIG. 9 shows a view of an analytical apparatus mounted on a platform. B) shows an enlargement of are A in a).

FIG. 10 a) shows the cut-outs on the platform and the screws for lowering them for arresting the units. b) is an enlargement of area B.

FIG. 11 shows an analytical apparatus comprising several units mounted on the platform with the units fixed to the platform and to neighboring units.

DETAILED DESCRIPTION OF THE INVENTION

Figure 1:
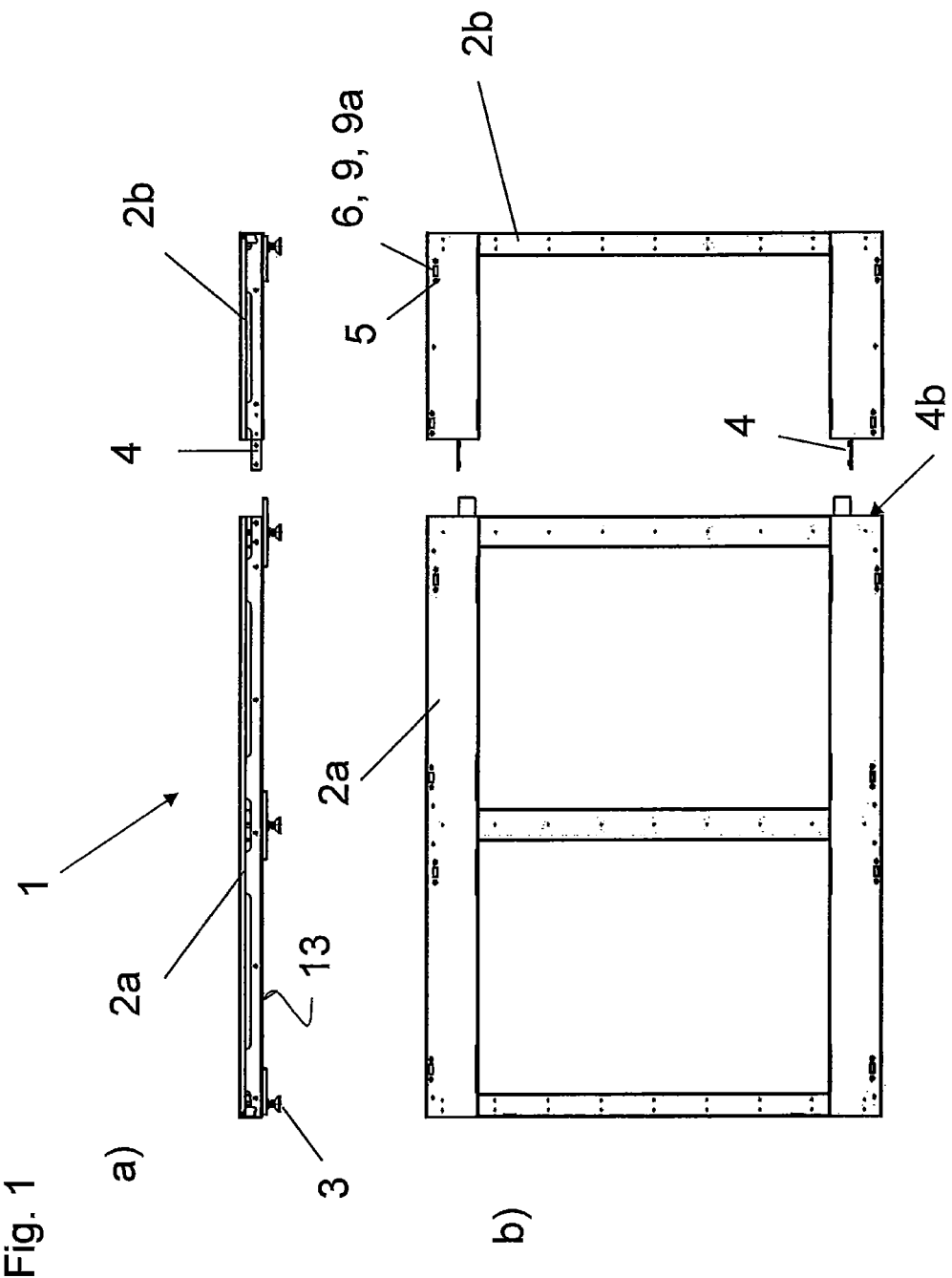
FIG. 1 shows a) a side and b) a top view of two platform elements before assembly.

The present invention relates to a method of mounting an analytical apparatus comprising at least two units. The claimed method comprises the steps of:
  placing a platform on a surface, wherein said platform comprises at least one platform element and multiple feet for placing the platform elements on a surface, wherein said feet are individually adjustable in height;
  adjusting the height of the platform before mounting and positioning of the units; and
  mounting and positioning the at least two units.

The term "analytical apparatus" as used herein relates to an apparatus which can perform at least parts of a method of analyzing an analyte. The term "analyte" is further defined below. Methods of analyzing an analyte may comprise dispensing liquid samples comprising an analyte, isolating and purifying an analyte, preparing reaction mixtures, reacting an analyte with reagents necessary to obtain a detectable signal etc.

The term "unit" as used herein relates to individual modules or cells or parts of an analytical apparatus which carry out specific parts of analysis of an analyte. Specific types of units are defined below.

The term "platform" as used herein relates to a platform or frame which is placed on a surface and on which an analytical apparatus is mounted.

The term "platform element" as used herein relates to a part of a platform. More than one element can be assembled to form a platform.

The term "feet" as used herein relates to elements of the platform which directly interact with the surface on which the platform is placed. A preferred embodiment of feet are actual feet which are mounted on the bottom surface of the platform.

The term "surface" as used herein relates to the surface on which the platform is placed for mounting of the analytical apparatus. The surface may include a floor of a laboratory or a table placed in a room etc.

The term "individually adjustable in height" as used herein relates to the capability of the feet to be adjusted up- or downwards independently of each other to ensure that the platform is even in the absence of the analytical apparatus and the apparatus is placed evenly on the platform after mounting on the adjusted platform.

The term "mounting" as used herein relates to the installation of the units of the analytical apparatus on the platform.

The term "positioning" as used herein relates to the mounting and placement of a unit in the position required for it to function within the analytical apparatus.

In a preferred embodiment, the platform comprises a first platform, and the method further comprises the steps of mounting a second platform on said first platform, wherein said second platform is movable on said first platform.

This has the advantage that the analytical apparatus can be moved away from the laboratory wall near which it is mounted if access is required for servicing from the back. A particular advantage of the movable mount is that the analytical apparatus can be mounted closer to the walls than would be required if it were not movable, since the distance from laboratory walls otherwise would include the necessary space providing access to service personnel. Thus, since the apparatus mounted on a movable platform can be placed more closely to the laboratory walls compared to a non-movable mount, the footprint in the laboratory required for mounting the apparatus is reduced compared to known mounts of analytical apparatuses.

Preferably, the method additionally comprises the step of positioning said units on said platform by placing bearing wheels comprised on said units in at least one cut-out comprised on said first and/or second platform. The term "cut-out" relates to an element on the platform which is constructed and arranged to arrest the moving elements on a unit. Preferred embodiments of cut-outs are described herein but are not limiting. While the bearing wheels allow moving a unit along the platform when mounting it, the cut-out in the platform allows to arrest the unit since the bearing wheels fall into the cut-out and can not move further. Said cut-out preferably comprises a plate with screws, wherein the screws allow lowering of the plate into an opening on the surface of the platform, thus forming the cut-out.

The mount of the apparatus is then preferably further strengthened by connecting one unit to a neighboring unit. Preferably, said connecting is achieved by connecting two neighboring units with a connecting element, more preferably a screw. More preferably, said method additionally comprises connecting said units to the platform. This further stabilizes the mounted apparatus. In a preferred embodiment of the method hereinbefore described, the step of mounting a unit comprises mounting at least one unit for isolating and purifying an analyte present in a liquid sample. More preferably additionally at least one unit for reacting said analyte with reagents necessary to obtain a detectable signal is mounted. Preferably, additionally at least one transport module is mounted. In a preferred embodiment, at least one unit for loading a sample into the analytical apparatus is additionally mounted. The units can be mounted in any order.

The term "isolating and purifying an analyte" as used herein relates to preparing an analyte for further analysis. The term is understood to comprise any method of preparing the analyte, including solid phase binding and washing of the analyte prior to further analysis.

The term "analyte" as used herein may be any type of biomolecule which is of interest for detection, and the detection thereof is indicative of a diagnostic status of an organism. The organism can be animal or, more preferably, human. Preferred analytes are proteins, polypeptides, antibodies or nucleic acids. More preferably, the analyte is a nucleic acid.

The term "liquid sample" as used herein relates to any type of liquid sample that may be obtained from an individual to perform an analytical test. Non-limited examples of liquid samples are urine, plasma, whole blood, serum, sputum, alveolar lavage etc.

The term "reacting" as used herein relates to any type of chemical reaction of the analyte with reagents that is necessary to obtain a detectable signal. Preferably, said reacting comprises amplification. Amplification may be understood as any type of enhancement of a signal. Thus, amplification can be a conversion of a molecule by an enzyme, wherein said enzyme is coupled or bound to the analyte, leading to a detectable signal, wherein more signal molecules are formed than analyte molecules are present. One such non-limiting example is a formation of a chemiluminescent dye, e.g. using ECL. The term amplification further relates to nucleic acid amplification, if the analyte is a nucleic acid. This includes both linear, isothermal and exponential amplifications. Non-limiting examples of nucleic acid amplification methods are TMA, SDA, NASBA, PCR, including real-time PCR. Such methods are well known to the skilled person.

The term "reagents" as used herein relates to any reagents necessary to perform an analytical method in the analytical apparatus. Such reagents may include reagents necessary for isolating and purifying an analyte, and/or reagents necessary for reacting the analyte to obtain a detectable signal.

The term "detectable signal" as used herein relates to signals obtained with the analytical method to determine the presence or absence of the analyte, or to quantitate the analyte. Non-limiting examples for such detectable signals are chemiluminescence or fluorescence or other stainings.

The term "transport module" as used herein relates to a module or unit or cell which can transport items between the units of the analytical apparatus. Such items may, as non-limiting examples, be containers comprising reagents, consumables, liquids etc. Thus, the transport module is preferably constructed and arranged to transport items between the units of the analytical apparatus.

Further embodiments of the method hereinbefore described include any one or combination of features described below.

The invention further relates to a combination of an analytical apparatus comprising at least two units, and a platform on which said apparatus is mounted. The platform comprises at least one platform element and multiple feet for placing the platform elements on a surface, wherein said feet are individually adjustable in height.

In one embodiment, the platform comprises at least two platform elements, wherein said at least two platform elements are fixedly connected to each other. Preferably, said platform comprises a first platform and a second platform mounted on top of said first platform, wherein said second platform is movable on said first platform. The advantage of the movable platform is described above.

In one embodiment, said second platform comprises moving elements, preferably bearing wheels which run on said first platform.

In one aspect of the invention, the second platform comprises hydraulic cylinders connected to a hydraulic pump. Preferably, said hydraulic pump is connected to an electromotor. In case the motor is not working, it is preferred to also include a crank connected to the hydraulic pump to allow the user to move the analytical apparatus mounted on the second platform manually.

In one aspect of the invention, the units comprise bearing wheels. These allow mounting of the units on the platform by moving them over the platform.

In one embodiment of the invention, first or second platform comprises at least one cut-out for positioning said units on said platform by placing said bearing wheels in said cut-out. This allows for proper positioning of the units on the platform.

In one aspect of the invention, the apparatus comprises at least one unit. In a preferred embodiment, it comprises:
- at least one unit for loading a liquid sample into the analytical apparatus; and/or
- at least one unit for isolating and purifying an analyte present in a liquid sample; and/or
- at least one unit for reacting said analyte with reagents necessary to obtain a detectable signal; and/or
- at least one transport module.

In a preferred embodiment, the analytical apparatus or method are fully automated.

In one embodiment, the apparatus further comprises a unit for preparing a reaction for a cyclic reaction of an analyte with reagents necessary to perform the cyclic reaction. Preferably, said cyclic reaction is nucleic acid amplification.

The apparatus may additionally comprise a detection module.

Non-limiting examples of preferred embodiments of the present invention are shown in FIGS. 1 to 11.

Figure 2:
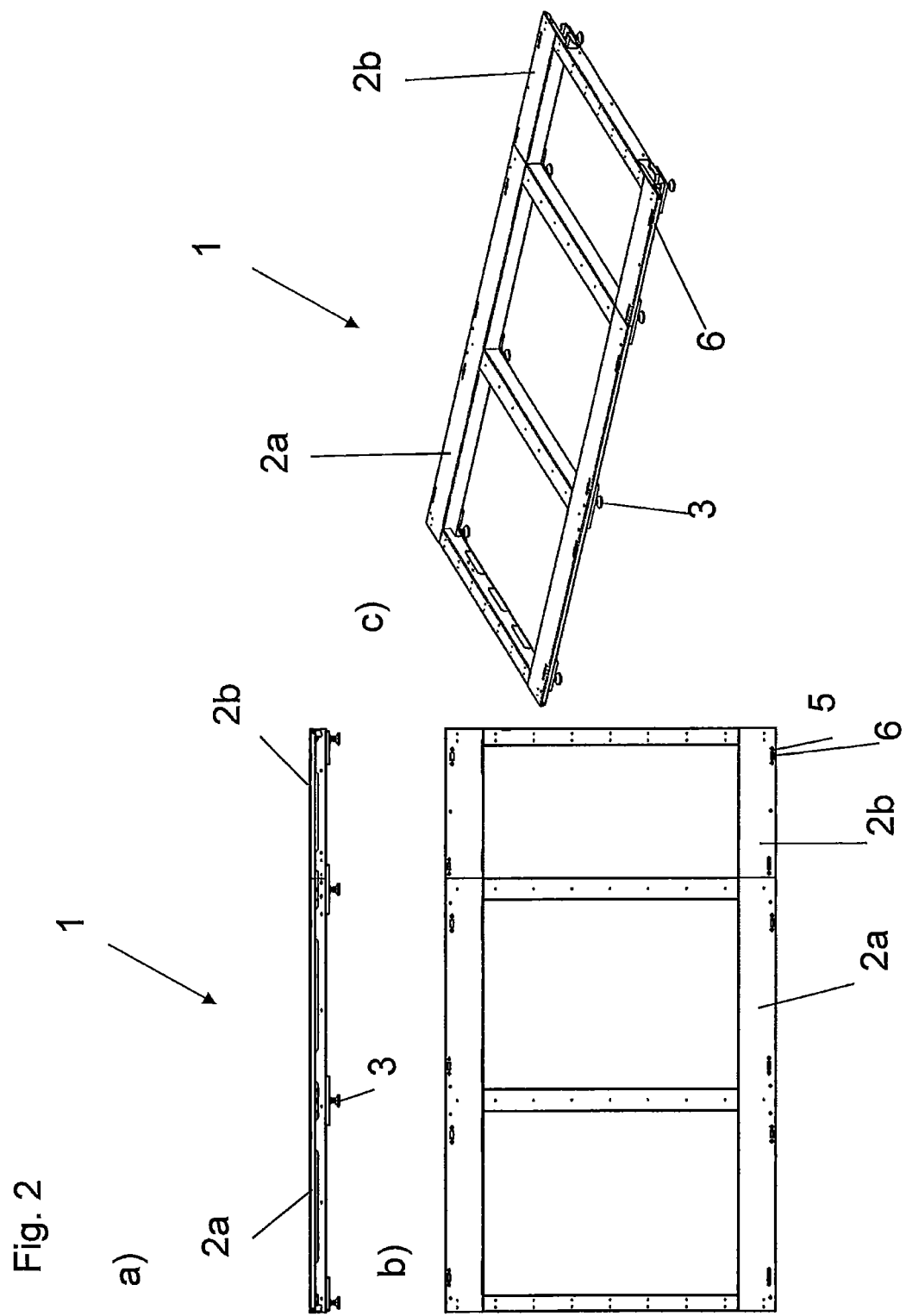
FIG. 2 shown a) a side vire, b) a top view and c) a perspective view of a platform assembled from two platform elements.
Figure 3:
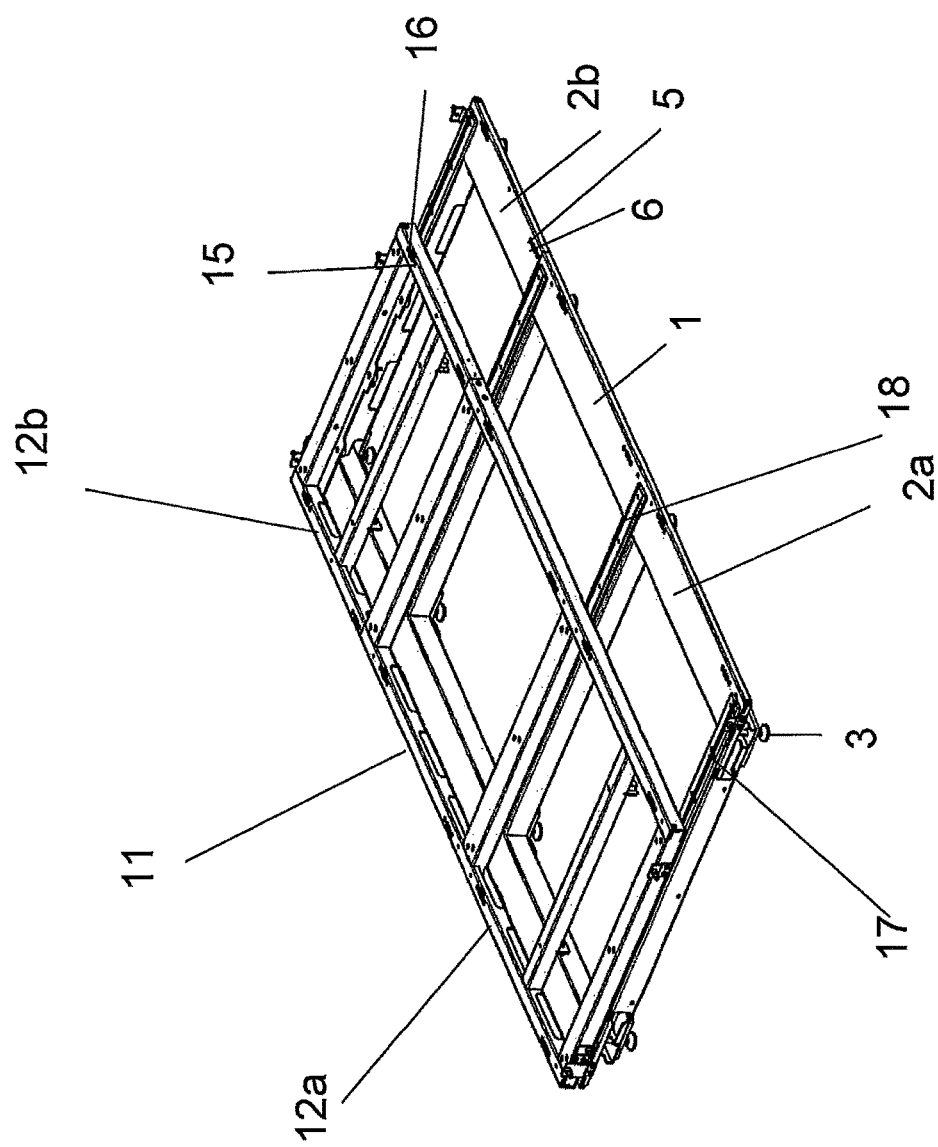
FIG. 3 shows a second platform mounted on a first platform.
Figure 4:
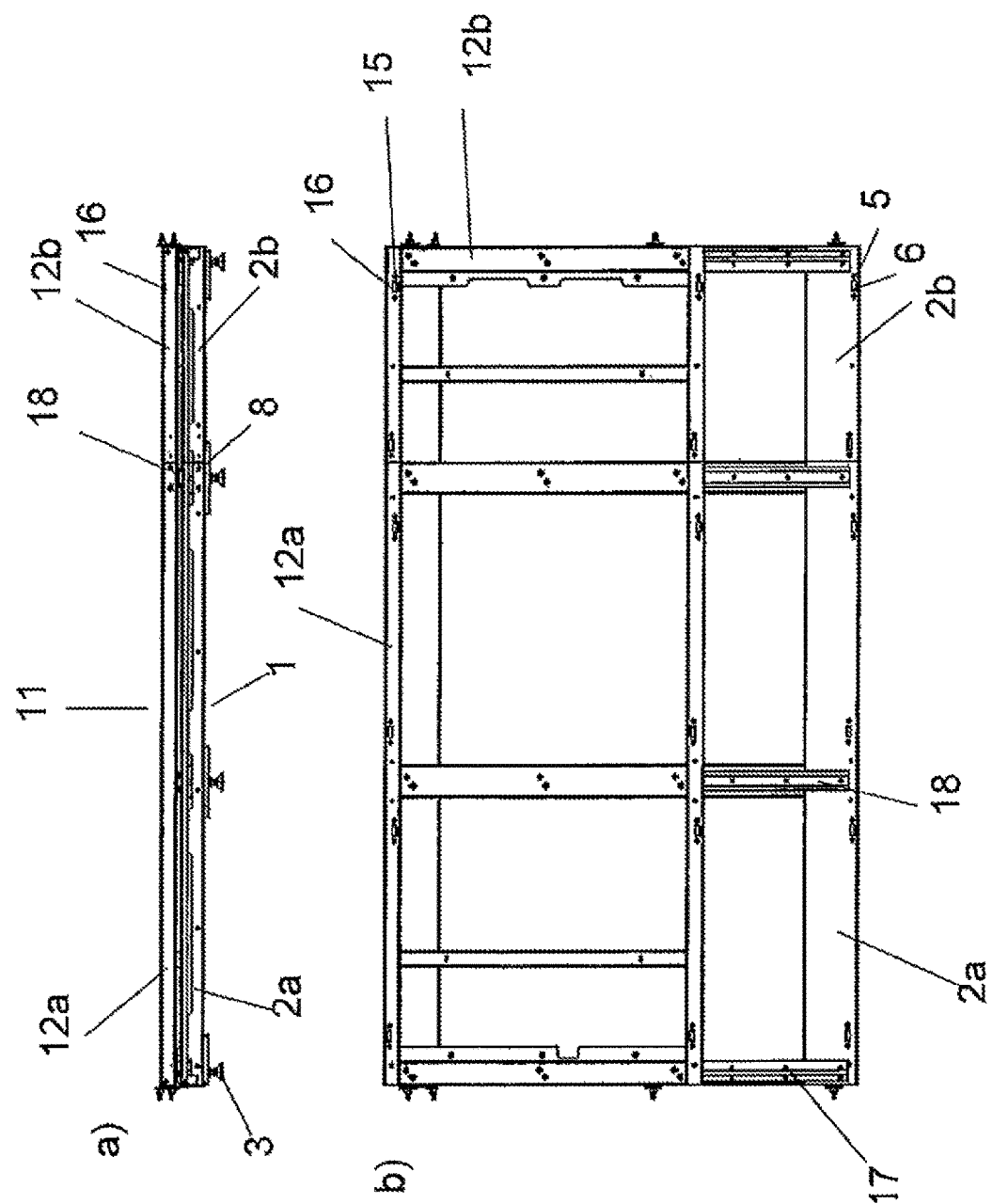
FIG. 4 shows a) a side and b) a top view of a second platform mounted on a first platform.
Figure 5:
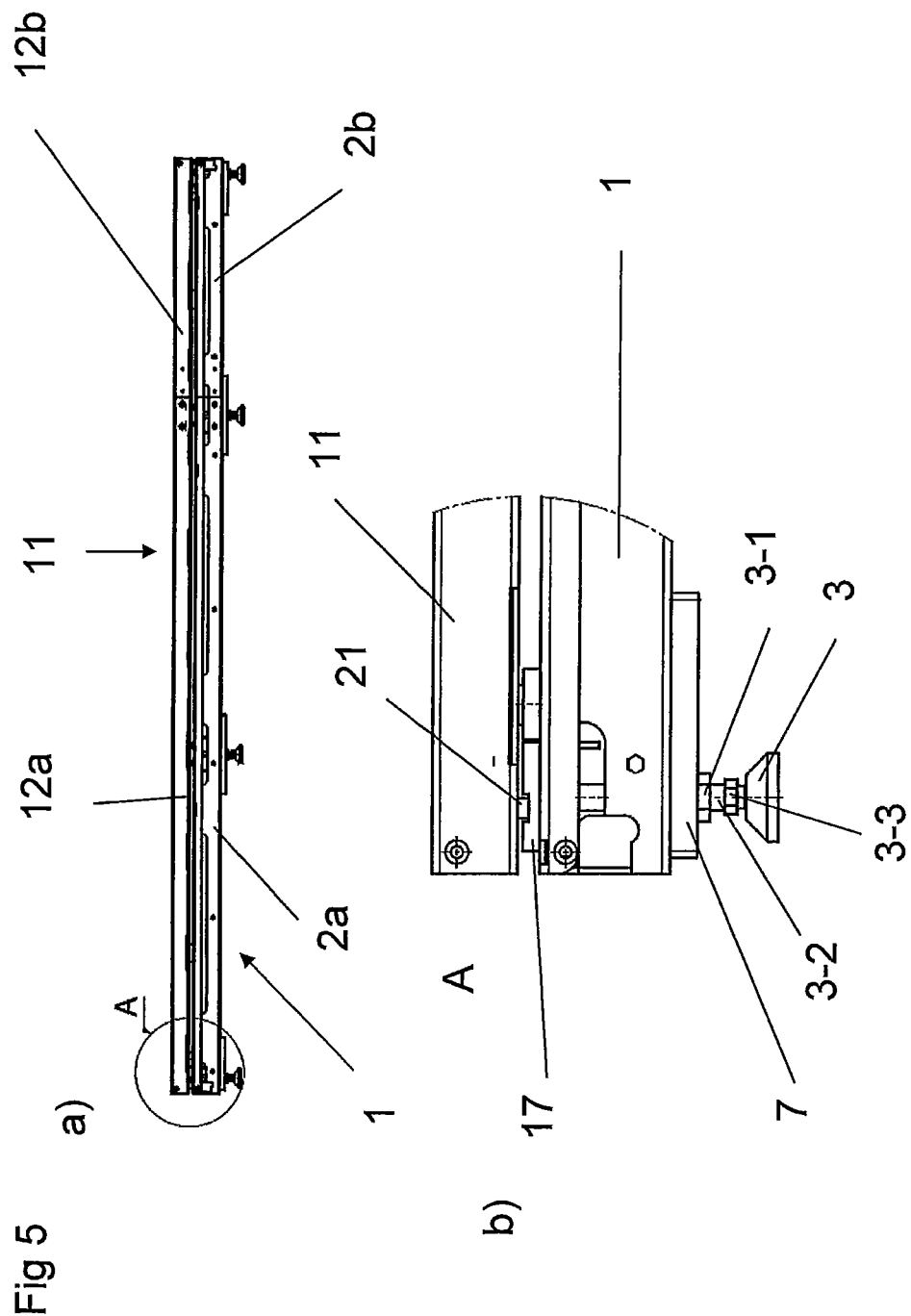
FIG. 5 shows a) a side view of a second platform mounted on a first platform, and b) an enlargement of area A.

FIG. 1a) shows a side view, and FIG. 1 b) a top view of a platform (1) according to the present invention. The platform (1) comprises a first platform element (2a) and a second platform element (2b). The platform elements shown on FIG. 1 are separate. A connecting element (4) is shown on platform element (2b). This connecting element (4) can be moved into a receiving part (4b) of platform element (2a). The two platform elements (2a) and (2b) are then fixed by screws (8) to form platform (1). FIG. 2 shows the two platform elements (2a) and (2b) fixed together. Feet (3) are mounted on the bottom side (13) of the platform and are height adjustable. Any one foot (3) has a internal thread (3-1) and an external thread (3-2) for height-adjustment. The feet (3) also comprise a contact element (3-3) for interfacing with a wrench. This makes it possible to adjust the height of the platform (1) prior to mounting the units (40, 41, 42, 43).

Figure 6:
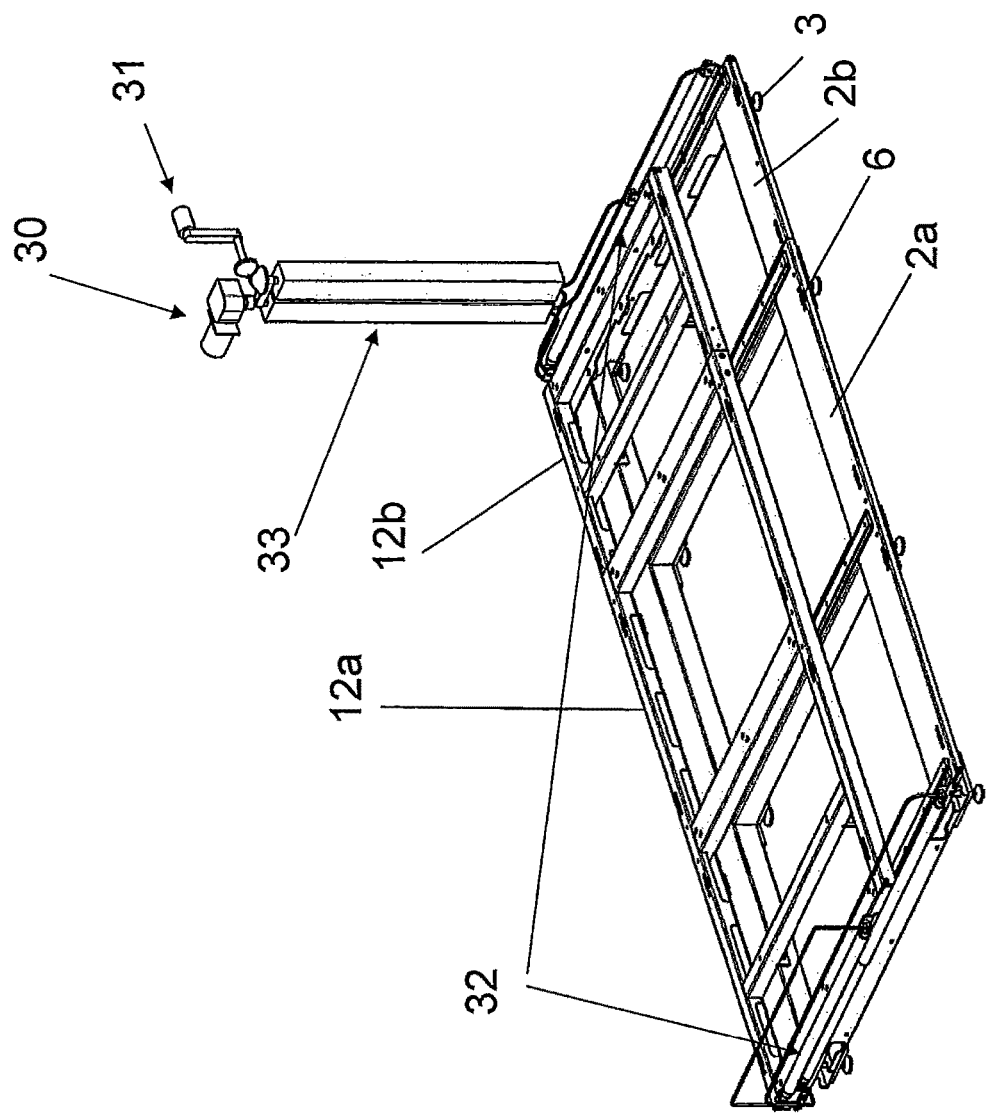
FIG. 6 shows a view of a second movable platform mounted on a first platform and the electromotor, crank and hydraulic pump to move the second platform on the first platform automatically or manually.

One embodiment of the platform comprises a second platform (11) mounted on the first platform (1) (FIGS. 3 to 6). The second platform (11) preferably also comprises at least one platform element. In the embodiment shown in FIG. 3, the platform comprises platform element (12a) and platform element (12b) which are assembled in the same way as platform elements (2a) and (2b). The first platform (1) comprises gliding elements (17, 18). The second platform comprises moving elements (21), preferably bearing wheels (21), which interact with the moving elements (17, 18), which are preferably rails, of the first platform. This allows the second platform (11) to move on the first platform (1). One embodiment of a moving mechanism is shown in FIG. 6. The platform may be moved by an actuator, more preferably an electromotor (30) connected to a hydraulic pump (33). The second platform (11) comprises hydraulic cylinders (32) connected to the hydraulic pump (33). Preferably, crank (31) is also included which allows the user to move the second platform if the motor (30) is not working. The movement of units (40) is shown in FIG. 7. The second platform (11) also comprises screws (15) which correspond to screws (5), small plates (16) which correspond to small plates (6) and cut-outs (19) comprising openings (19a) which correspond to cut outs (9) and openings (9a).

Once the platform (1, 11) is mounted and the height of the feet is adjusted, the units can be mounted on the platform (1). The units (40, 41, 42) comprise bearing wheels (21) on the underside (49) of the units. The bearing wheels (21) glide on the platform until they fall into a cut-out (9). Cut-out (9) is preferably a small plate (6) which can be lowered into an opening (9a) of the platform with screws (5). Thus, plates (6) are lowered to form a cut-out (9) in only those positions where it is desired that the bearing wheels (21) are arrested in the cut-out (9). Once the first unit (42) is thus fixed, the next unit (41) can be mounted (FIG. 8, 10). In order to prevent sideways movement of the units (40) during mounting on the platform (1), a side guidance (23) is comprised on the platform, and a side guidance (22) is comprised on the unit (40).

Mounting of the units (40) on the second platform (11) is essentially performed like the mounting on the first platform (1).

Once all the units (40, 41, 42, 43) are mounted on the platform (1), the units are fixed to the platform (1) with connecting elements (52), which are preferably screws (52). The units (40, 41, 42, 43) are also connected neighboring units (40, 41, 42, 43) with connecting elements (51), preferably with screws (51).

In a preferred embodiment of the invention, the material of the platform is steel.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. An analyzer assembly platform comprising:
   at least two units configured for performing analysis on a fluid sample, the at least two unit including a plurality of bearing wheels on the underside of each of said units;
   a first platform, said first platform comprises
      a first platform element having a connecting element, a bottom surface with several individual height adjustable feet for placing said first platform element on a worksurface and a top surface with plurality of rails attached thereto; and
      a second platform element having a receiving part configured to accept the connecting element of the first platform element, a bottom surface with several individual height adjustable feet for placing the second platform element on the worksurface, and a top surface with a plurality of rails attached thereto,
      wherein the first platform is formed by connecting the connecting element of the first platform element with the receiving part of the second platform element;
   and;
   a second platform, said second platform includes frame structure with a top surface that includes a plurality of cut-outs, each of said plurality of cut-outs formed by a plate that can be lowered into the frame structure of said second platform by screws on the top surface of said second platform, the second platform includes a bottom surface having bearing wheels attached thereto, wherein the rails of said formed first platform are configured to accept the bearing wheels of said second platform such that said second platform is movable on said formed first platform; and wherein the bearing wheels on the underside of each of said at least two units glide on said second platform until they fall into the plurality of cut-outs on the top surface of said second platform.

2. The analyzer assembly platform of claim 1, wherein said second platform comprises hydraulic cylinders connected to a hydraulic pump.

3. The analyzer assembly platform of claim 2, wherein said hydraulic pump is connected to an electromotor.

4. The analyzer assembly platform of claim 1, wherein said at least two units configured for performing analysis on a fluid sample comprises:

at least one unit for isolating and purifying an analyte present in a liquid sample; or at least one unit for reacting said analyte with reagents necessary to obtain a detectable signal; or at least one transport module.

\* \* \* \* \*